(12) United States Patent
Chen

(10) Patent No.: US 9,895,095 B2
(45) Date of Patent: Feb. 20, 2018

(54) DYNAMIC URINE MONITOR AND DYNAMIC URINE MONITORING INSTRUMENT

(71) Applicant: ZHUHAI WOMU ELECTRONIC CO., LTD., Zhuhai, Guangdong (CN)

(72) Inventor: Yun Chen, Guangdong (CN)

(73) Assignee: ZHUHAI WOMU ELECTRONIC CO., LTD., Zhuhai (CN)

( * ) Notice: Subject to any disclaimer, the term of this patent is extended or adjusted under 35 U.S.C. 154(b) by 445 days.

(21) Appl. No.: 14/779,966

(22) PCT Filed: Sep. 29, 2012

(86) PCT No.: PCT/CN2012/082407
§ 371 (c)(1),
(2) Date: Sep. 24, 2015

(87) PCT Pub. No.: WO2014/036769
PCT Pub. Date: Mar. 13, 2014

(65) Prior Publication Data
US 2016/0051177 A1    Feb. 25, 2016

(30) Foreign Application Priority Data
Sep. 7, 2012    (CN) .......................... 2012 1 0331329

(51) Int. Cl.
*A61B 5/20*    (2006.01)
*A61B 10/00*    (2006.01)
(Continued)

(52) U.S. Cl.
CPC ............ *A61B 5/208* (2013.01); *A61B 5/0004* (2013.01); *A61B 5/6891* (2013.01);
(Continued)

(58) Field of Classification Search
CPC ..... A61B 5/6891; A61B 5/208; A61B 5/7225; A61B 10/007; A61B 5/0004; G01N 33/493
See application file for complete search history.

(56) References Cited

U.S. PATENT DOCUMENTS 2,822,803 A * 2/1958 Huxley, III ............ A61G 11/00
601/43
3,410,107 A * 11/1968 Wallace ................. A61G 10/04
128/204.15
(Continued)

FOREIGN PATENT DOCUMENTS

CN    1039656 A    2/1990
CN    101806697 A    8/2010
(Continued)

OTHER PUBLICATIONS

International Search Report of PCT Patent Application No. PCT/CN2012/082407 dated Jun. 20, 2013.
(Continued)

*Primary Examiner* — Michael C Stout

(57) ABSTRACT

This invention provides a dynamic urine monitor. The dynamic urine monitor comprises a case, inside which is equipped with a urine collection device, a pipeline for flowing the urine into the urine collection device, and a measurement system for dynamically measuring the urine. The measurement system comprises a weight measurement subsystem, a density measurement subsystem, and an outlet-inlet module. The weight measurement subsystem comprises a weight sensor and a weight information ADC; the weight sensor dynamically measures the urine weight of the urine collection device. The density measurement subsystem comprises a density sensor and a density information ADC. The density sensor dynamically measures the urine density and it is serially connected with the upstream pipeline of the (Continued)

urine collection device. The outlet-inlet module is used to exchange the information of the weight information ADC and with density information ADC with outside.

20 Claims, 8 Drawing Sheets

(51) Int. Cl.
  *A61B 5/00*   (2006.01)
  *G01N 33/493*   (2006.01)
  *G01N 9/24*   (2006.01)
(52) U.S. Cl.
  CPC ............ *A61B 5/7225* (2013.01); *A61B 5/742* (2013.01); *A61B 10/007* (2013.01); *G01N 33/493* (2013.01); *A61B 2560/0475* (2013.01); *A61B 2562/0271* (2013.01); *G01N 9/24* (2013.01)

(56) References Cited

U.S. PATENT DOCUMENTS

| | | | | |
|---|---|---|---|---|
| 4,557,453 A | * | 12/1985 | McCloskey | A61G 7/05 248/283.1 |
| 4,664,124 A | | 5/1987 | Ingle et al. | |
| 5,161,764 A | * | 11/1992 | Roney | A61M 5/1415 248/218.4 |
| 5,198,192 A | * | 3/1993 | Saito | A61B 5/14532 4/314 |
| 5,596,948 A | * | 1/1997 | Ritchie | A01K 1/031 119/417 |
| 5,730,149 A | * | 3/1998 | Nakayama | A61B 10/007 600/573 |
| 5,829,723 A | * | 11/1998 | Brunner | A61M 5/1413 248/222.13 |
| 7,376,992 B2 | * | 5/2008 | Salt | A61G 1/04 5/503.1 |
| 7,398,951 B1 | * | 7/2008 | Sugalski | A61G 7/0503 248/214 |
| 8,302,231 B2 | * | 11/2012 | Moffitt | A61G 1/04 5/503.1 |
| 2001/0011166 A1 | * | 8/2001 | Harper | A61M 1/0021 604/322 |
| 2003/0070236 A1 | * | 4/2003 | Barker | A61B 5/00 5/658 |
| 2003/0149408 A1 | * | 8/2003 | Levinson | A61B 10/007 604/329 |
| 2005/0247121 A1 | * | 11/2005 | Pelster | A61B 5/208 73/223 |
| 2006/0096017 A1 | * | 5/2006 | Yamasaki | E03D 9/05 4/420 |
| 2007/0179389 A1 | * | 8/2007 | Wariar | A61B 5/14507 600/508 |
| 2007/0215782 A1 | * | 9/2007 | Phung | A61G 7/0503 248/691 |
| 2008/0004576 A1 | * | 1/2008 | Tanaka | A61B 5/208 604/317 |
| 2008/0312550 A1 | * | 12/2008 | Nishtala | A61B 5/14507 600/549 |
| 2009/0237264 A1 | * | 9/2009 | Bobey | A61G 7/05776 340/815.69 |
| 2010/0137743 A1 | * | 6/2010 | Nishtala | A61B 5/14507 600/575 |
| 2010/0211070 A1 | * | 8/2010 | Subramaniam | A61B 18/1206 606/49 |
| 2011/0121149 A1 | * | 5/2011 | Herskovic | A61G 7/0503 248/223.41 |
| 2013/0245498 A1 | * | 9/2013 | Delaney | A61B 5/742 600/584 |

FOREIGN PATENT DOCUMENTS

| | | |
|---|---|---|
| CN | 102288516 A | 12/2011 |
| CN | 202793546 U | 3/2013 |
| JP | 2001296293 A | 10/2001 |
| JP | 2003042913 A | 2/2003 |

OTHER PUBLICATIONS

1st Office Action of counterpart Chinese Patent Application No. 201210331329.7 dated Mar. 5, 2014.
2nd Office Action of counterpart Chinese Patent Application No. 201210331329.7 dated Aug. 5, 2014.

* cited by examiner

DYNAMIC URINE MONITOR AND DYNAMIC URINE MONITORING INSTRUMENT

CROSS-REFERENCE TO RELATED APPLICATIONS

The present application is a national phase entry under U.S.C. § 371 of International Application No. PCT/CN2012/082407 filed on Sep. 29, 2012, which claims priority from Chinese patent application No. 201210331329.7 filed on Sep. 7, 2012, all of which are hereby incorporated by reference herein.

TECHNICAL FIELD

The invention relates to a medical instrument. More particularly, the invention relates to a monitor and a monitoring instrument which is used to dynamically measure urine.

TECHNICAL BACKGROUND

Urine flow is an important indicator for the dynamic equilibrium of body fluid and functions of heart and kidney. Accurate monitoring of urine flow can assist in judging the development of diseases and in making a treatment plan. Monitoring urine flow is one of the important measures to examine the patient. For critically ill patients, urine flow can often predict kidney disorder before the blood creatinine elevates. Although clinical monitoring of urine flow is an important test which can timely reveal the human body's effective blood circulation and the kidney function, the accuracy and timeliness of the test are by far insufficient; even less attention has been paid to safe and automatic monitoring of urine. Currently, the urine tests for critically ill patients are performed manually and intermittently. This not only increases the workload of the nurses and results in unnecessary costs, but also increases the risk of urine contamination. Furthermore, it may cause delay and mistake in clinical judgments and serious errors.

Also, urine density reflects the concentration function of kidney. A high urine density may relate to dehydration, albuminuria, saccharorrhea, acute nephritis, and high fever etc. A low urine density may indicate problems with kidney concentration function, such as chronic renal glomerulus nephritis, acute nephritis polyuria time, and uremia polyuria time etc. Urine density monitoring is usually performed by intermittently manual sampling and then testing the samples by an instrument. Because of the time gap between the sampling and the testing, urine samples which are not tested quickly may produce precipitations, which result in testing results errors.

Technical Problems

The above-mentioned intermittent monitoring no longer satisfies the needs for digitalization of the modern clinic medical practices. Therefore, new dynamic urine monitors and urine monitoring instruments for real-time measurements of urine flow and urine density are needed.

Technical Solutions

The main objective of the invention is to provide a dynamic urine monitor for urine flow and urine density measurements.

Another objective of the invention is to provide a dynamic urine monitor in which the pipeline and the testing system can be flushed after they are used.

Still another objective of the invention is to provide a dynamic urine monitor which can be conveniently fixed on the patient's bed.

Still another objective of the invention is to provide a dynamic urine monitor which can be conveniently moved.

Still another objective of the invention is to provide a dynamic urine monitor which can collect fresh urine samples.

Another main objective of the invention is to provide a dynamic urine monitoring instrument which comprises the above-mentioned dynamic urine monitor.

To achieve the above-mentioned main objective, this invention provides a new dynamic urine monitor. The dynamic urine monitor comprises a case; equipped inside the case are a urine collection device, a pipeline for introducing and flowing urine into the urine collection device, and a measurement system for dynamic measurement of the urine. The measurement system comprises a weight measurement subsystem, a density measurement subsystem, and an outlet-inlet module. The weight measurement subsystem comprises a weight sensor, and a weight information Analogue-to-Digital Converter (ADC); the weight sensor is connected with the urine collection device and is used to dynamically measure the weight of the urine in the urine collection device. The density measurement system comprises a density sensor and a density information Analogue-to-Digital Converter (ADC). The density sensor is used to dynamically measure the urine density; it is serially connected in the upstream pipeline of the urine collection device. The outlet-inlet module is used to perform data exchange for the weight information ADC and the density information ADC with outside equipment.

A more detailed scheme of the above measurement system also comprises a master control module. The master control module is equipped with an information storage element which is used to store information from the weight information ADC and the density information ADC.

According to the above scheme, when the dynamic urine monitor is not connected with outside equipment, the information from the weight information ADC and the density information ADC can be stored in the information storage element. When the dynamic urine monitor is connected with outside equipment, the master control module will first pass on the information stored in the information storage element and then pass on the information of the weight information ADC and the density information ADC. When the dynamic urine monitor is not connected with outside equipment, the information can be obtained from the information storage element.

Another more detailed scheme is that the pipeline comprises an overflow path which is linked in parallel with the two ends of the density sensor. When the urine flow of the patient is too high, a portion of the urine will flow from the overflow path into the urine collection device without flowing through the density sensor. When the urine flow of the patient becomes normal, the urine will then pass through the density sensor and flow into the urine collection device.

Preferably, the inside of the case is equipped with a washing device. The washing device comprises a water pump. The water pump is connected with a water inlet pipe and a water outlet pipe. The water outlet pipe is connected with the density sensor. When monitoring is complete, the density sensor is flushed with water via the water pump and the waste water flows into the urine collection device. The urine collection device is then removed and replaced for the next monitoring. Therefore, the other objective of the invention is achieved by this scheme; this scheme also prevents microbes from growing inside the pipeline and the density sensor.

A relatively detailed scheme is that inside the case is equipped with a water container which is connected with the water inlet pipe. The water container makes the operation easier because the water pump does not have to pump water from outside the dynamic urine monitor. Preferably, the water container holds enough water for one or two flushes.

A more detailed scheme is that the water container is equipped with a water level detector. The water level detector is linked to an alarm. When the water level in the water container becomes low, the alarm sounds the warning; water can be then added to the water container to prevent the water pump from running without water.

Preferably, the dynamic urine monitor is equipped with a fixing device. The fixing device comprises a fixing clip which can hang on a crossbeam of the patient's bed. On the case is equipped with a guiding mechanism which guides the fixing device to freely slide along the vertical direction. The fixing clip fixes the dynamic urine monitor on the crossbeam of the patient's bed. The position of the fixing clip can be adjusted along the vertical direction via the guiding mechanism. Therefore, the dynamic urine monitor can be conveniently put on or removed from the patient's bed and can be used for various patients' beds of different height. The other objective of the invention is thus achieved.

A relatively detailed scheme is that the fixing device comprises a sliding board which can slide within the guiding device, a supporting pole which has one end fixed on the sliding board, a fixing clip which can slide along the supporting pole, and a first fixing knob which is used to fix the fixing clip against the supporting pole. The vertical height of the device can be adjusted through the sliding board of the sliding mechanism and its horizontal position can be adjusted through the sliding along the supporting pole. Therefore, the dynamic urine monitor can be conveniently connected with and removed from the patient's bed.

A more detailed scheme is that both sides of the case are equipped with the guiding mechanisms, both ends of the sliding board are restricted within the guiding mechanisms of the two sides, and there are two symmetric supporting poles, fixing clips, and first knobs. The use of two supporting poles, two fixing clips, and two first fixing knobs can help to fix the dynamic urine monitor more firmly on the crossbeam; the sliding board makes the two supporting poles remain on the same horizontal level.

A further detailed scheme is that the fixing clip is equipped with a second fixing knob. The second fixing knob fixes the dynamic urine monitor more firmly on the crossbeam.

Preferably, the bottom part of the case is equipped with wheels. The wheels make the dynamic urine monitor easy to move; and thus another objective of the invention is achieved. Because the dynamic urine monitor is fixed on the crossbeam of the patient's bed, when the bed moves, the dynamic urine monitor moves with it; therefore, the dynamic urine monitor can continuously work without the need for disconnection and reconnection. This reduces the workload of the hospital workers.

Preferably, the urine collection device comprises a first container in the upstream and a second container in the downstream. The first container and the second container are connected by a reversed U-shaped tube. The first container is equipped with a valve which can release the urine inside the container. When the urine in the first container reaches a certain level, the urine flows from the first container to the second container through the reversed U-shaped tube. Therefore, the urine in the first container will not stay too long; when sampling urine through the valve, the urine samples will be fresh. Another objective of the invention is thus achieved.

A relatively detailed scheme is that the case on a position facing the valve is equipped with a front cover gate. The front cover gate can make more convenient to sample the urine.

Preferably, the measurement system comprises a temperature measurement subsystem. The temperature measurement subsystem comprises a temperature sensor which locates at the entrance of the pipeline. By measuring the urine temperature, the body temperature of the patient can be monitored. When the dynamic urine monitor is linked with outside equipment, the urine temperature can be observed; and thus any abnormal change in the patient's body temperature can be timely discovered. Additional body temperature measurements will no longer be needed and it thus reduces the workload of the hospital workers.

To achieve the other main objective of the invention, the invention provides a dynamic urine monitoring instrument which comprises at least one dynamic urine monitor. The dynamic urine monitor comprises a case inside which is equipped with a urine collection device for collecting urine, a pipeline for flowing urine into the urine collection device, and a measurement system for dynamically measuring urine. The measurement system comprises a weight measurement subsystem, a density measurement subsystem, and an outlet-inlet module. The weight measurement subsystem comprises a weight sensor and a weight information ADC; the weight sensor is connected with the urine collection device and is used to dynamically measure the weight of the urine in the urine collection device. The density measurement system comprises a density sensor and a density information ADC. The density sensor is used to dynamically measure the urine density; it is serially connected in the upstream pipeline of the urine collection device. The outlet-inlet module is used to carry on data exchange for the information from the weight information ADC and the density information ADC with a treatment device. The treatment device comprises an information receiving module, a data treatment module, and a display monitor. The information receiving module receives the information from the outlet-inlet module. The data treatment module carries on calculations according to the information received by the information receiving module. The data treatment module comprises a urine flow rate calculation sub-module. The display monitor displays the urine density information from the information receiving module and the calculation results from the data treatment module.

A relatively detailed scheme is that the outlet-inlet module is a wireless transmitting module and the information receiving module is a wireless receiving module.

According to the above scheme, the outlet-inlet module and the information module exchange data between them via wireless transmission. Therefore, the treatment device and the dynamic urine monitor can be placed separately and it is convenient to observe the measurement results. Alternatively, the dynamic urine monitor and the treatment device can communicate through wire transmission and the treatment device can be equipped on the dynamic urine monitor; the display monitor can be placed on a position which can be easily observed.

The data treatment module may also comprise a urine osmotic pressure calculation sub-module. The urine density information from the density sensor can be converted into urine osmotic pressure information via the urine osmotic pressure calculation sub-module. The urine osmotic pressure information can be directly shown on the display monitor; no extra complex calculation is needed. Urine osmotic pressure is also important data in clinic medical practice; abnormalities of urine osmotic pressure may reveal changes of patient's health.

The data treatment module may also comprise a urine flow rate calculation sub-module. The dynamic urine flow rate information can be shown on the display monitor. The urine flow rate calculation sub-module converts the urine weight and urine density into urine flow rate; the dynamic urine flow rate can be directly shown on the display monitor; no extra calculation is needed.

The data treatment module may also comprise a urine concentration calculation sub-module; the urine concentration can be shown on the display monitor. The urine concentration calculation module converts the urine density from the urine density sensor into urine concentration and the urine concentration is directly shown on the display monitor; no extra calculation is needed. Urine concentration is also important data in the clinic medical science; its abnormality reveals changes of the patient's health; a real-time monitoring of the urine concentration is of importance.

The treatment system may comprise a remote management module. Through the remote management module, the patient's information can be monitored remotely and multiple patients can be monitored simultaneously in a control room.

Preferably, the data treatment system may also comprise a storage module which stores the information received by the information receiving module and the history of the calculation results from the data treatment module. Comparing the then-current information with historic information can help to judge the patient's health.

Effectiveness

According to the above schemes of the dynamic urine monitor of the invention, urine is introduced via the pipeline into the dynamic urine monitor, it flows through the density sensor wherein the dynamic urine density information is obtained, and it then flows into the urine collection device wherein the dynamic urine weight information is obtained. Therefore, dynamic measurements of urine weight and urine density are achieved. Further, the case of the dynamic urine monitor prevents the measurement system and the urine collection device from being interrupted by the working environment.

EMBODIMENTS OF THE INVENTION

The invention is further illustrated by the combination of the embodiments and the figures as follows.

Embodiment of the Dynamic Urine Monitor

Figure 1:
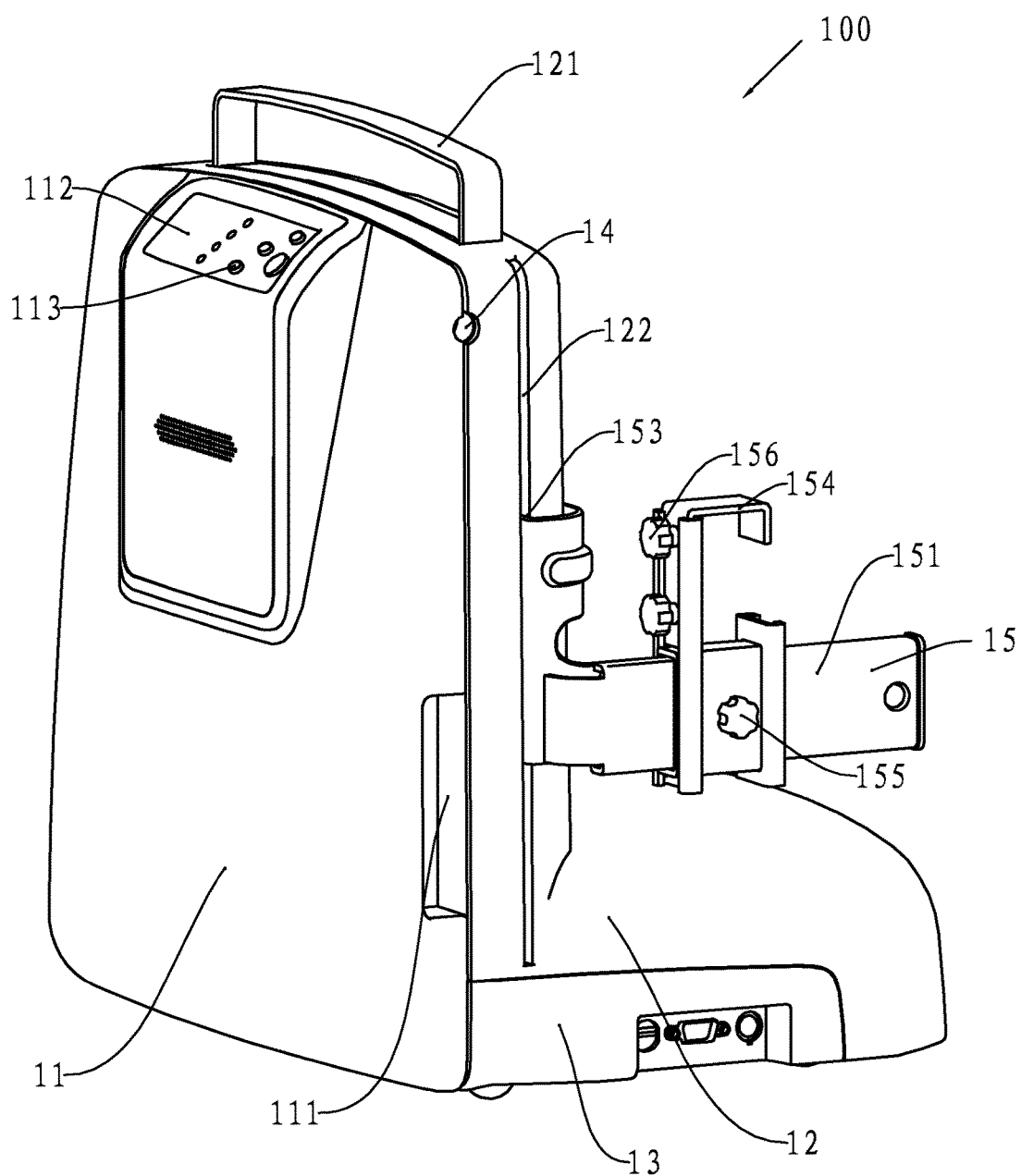
FIG. 1 is a three-dimensional view of the embodiment of the dynamic urine monitor of the invention.

The exterior structure of the dynamic urine monitor is shown in FIG. 1. The dynamic urine monitor 100 comprises a case which comprises a front cover gate 11, rear shell 12, and bottom shell 13. The measurement system is placed inside the case; a hole 14 which is used as the pipeline entrance is located on the upper portion of the right side of the case. The front cover gate 11 and the rear shell 12 are connected by a hinge joint and thus the front cover gate 11 can open or close to show or hide the measurement system inside the case. The right side of the front cover gate 11 has a notch 111 which is used as a handle to open or close the front cover gate 11. The upper portion of the front cover gate 11 is equipped with a control plane 112; the control plane 112 is equipped with a control push-button 113. The top portion of the rear shell 12 is equipped with an extendable handle 121; the extendable handle 121 is pulled out when it is used to move the dynamic urine monitoring instrument 100; when the dynamic urine monitoring instrument 100 is settled, the handle 121 is retracted to save space. The rear shell 12 is also equipped with a fixing device 15 which fixes the dynamic urine monitoring instrument on the crossbeam of the patient's bed.

Figure 2:
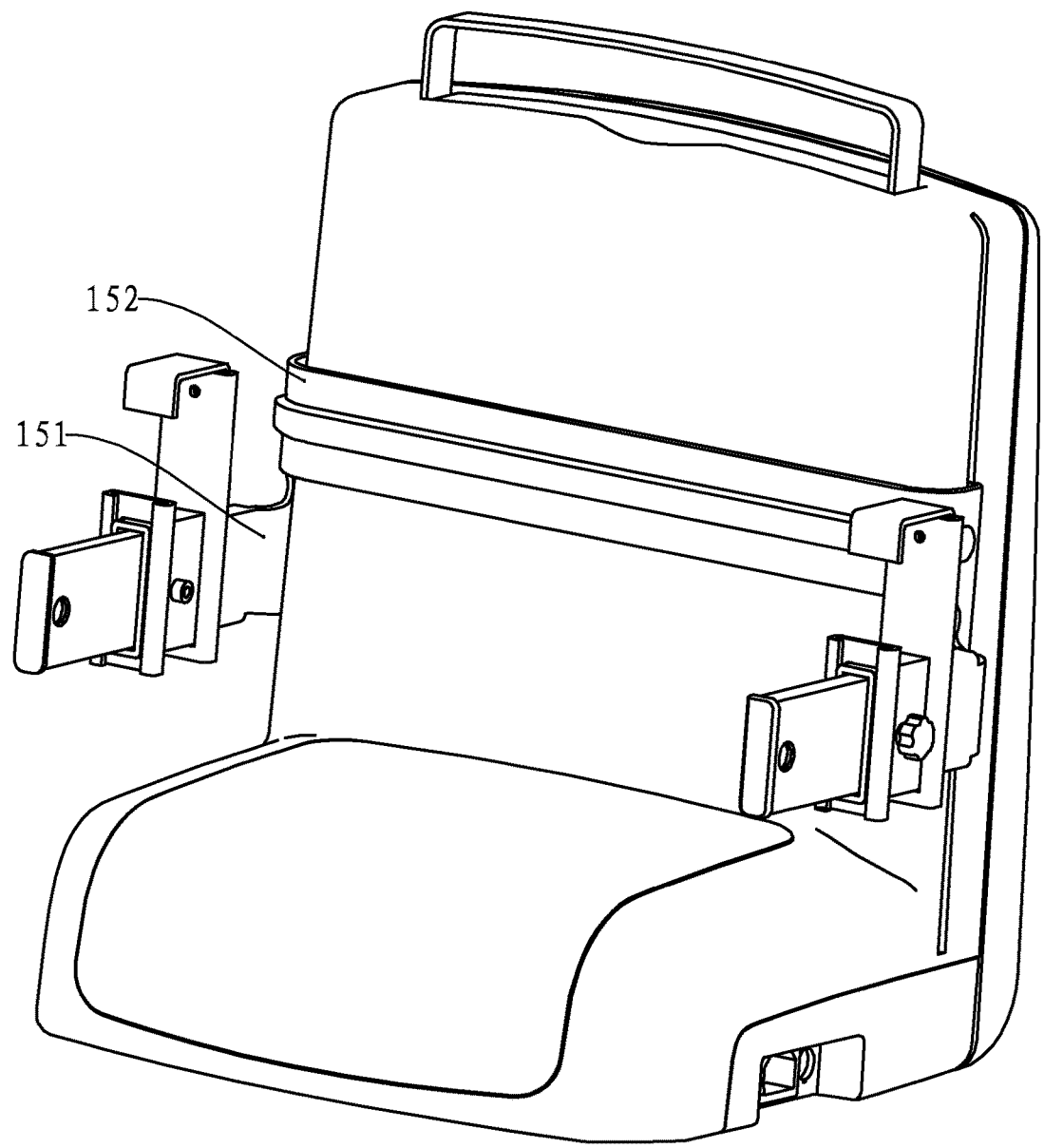
FIG. 2 is a three-dimensional view of the embodiment of the dynamic urine monitor of the invention from a different angle.

As shown in FIG. 1 and FIG. 2, the fixing device 15 comprises a supporting pole 151 which is set on both sides of the rear shell 12. The ends of the supporting poles 151 are linked with the sliding board 152. The end of the sliding poles is equipped with a flange 153 which extends toward the case. The flange 153 is restricted within a notch 122; the notch 122 is on the two sides of the rear shell 12 and is used as a guiding mechanism so that the fixing device 15 can slide relative to the case in the vertical direction to adjust the height of the fixing device 15. The supporting pole 151 is equipped with a fixing clip 154 which can slide in the horizontal direction along the supporting pole 151. When the fixing clip 154 needs to be fixed with the supporting pole 151, the fixing knob 155 (as a first fixing knob) can be revolved. A second fixing knob 156 can also be equipped on the fixing clip 154 to fix the fixing clip 154 with a bottom crossbeam of the patient's bed. It is understood that the case is equipped with a raised flange; the sliding board 152 has a notch and the coordination of the flange and notch allows the fixing device 15 to move in the vertical direction.

Figure 3:
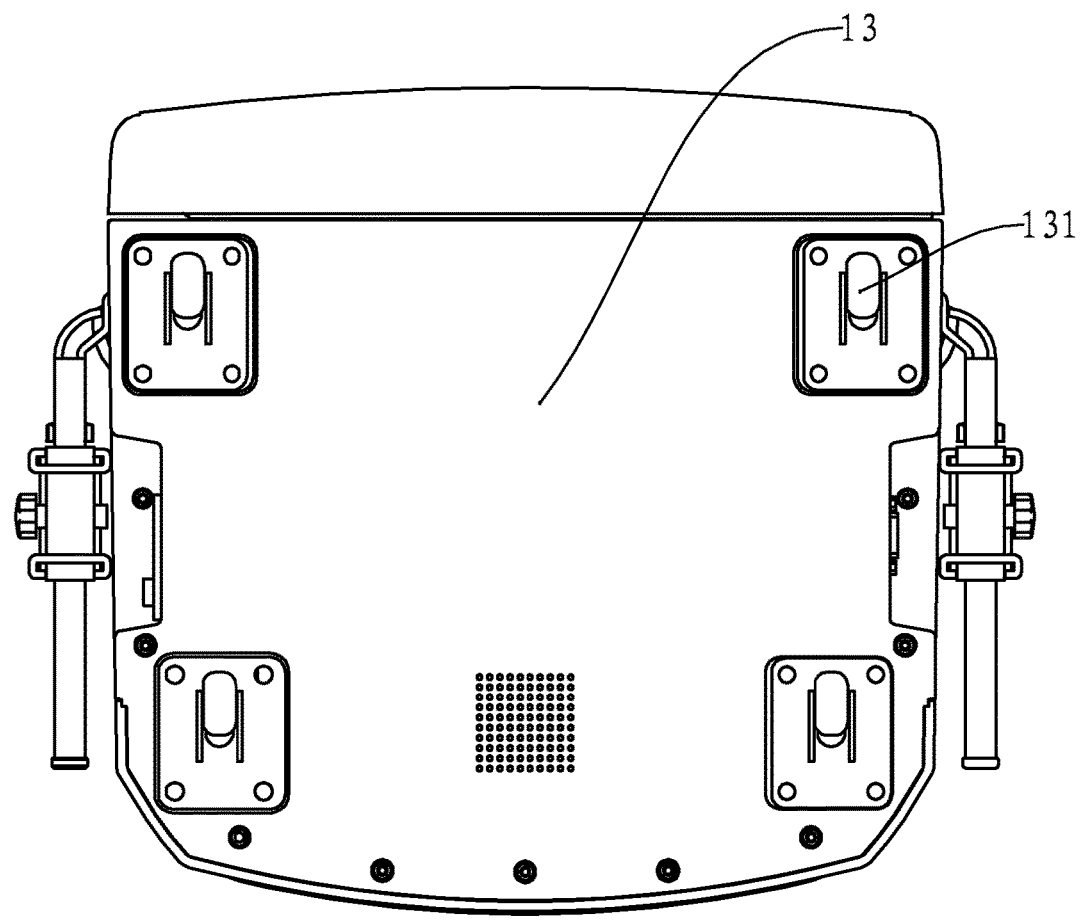
FIG. 3 is a bottom view of the embodiment of the dynamic urine monitor of the invention.

The bottom structure of the dynamic urine monitoring instrument is shown in FIG. 3. Four Omni-directional wheels 131 are provided on the bottom shell 13. The dynamic urine monitoring instrument 100 can be moved via these Omni-directional wheels 131. The bottom shell is also equipped with electricity plugs and USB plugs etc.

Figure 4:
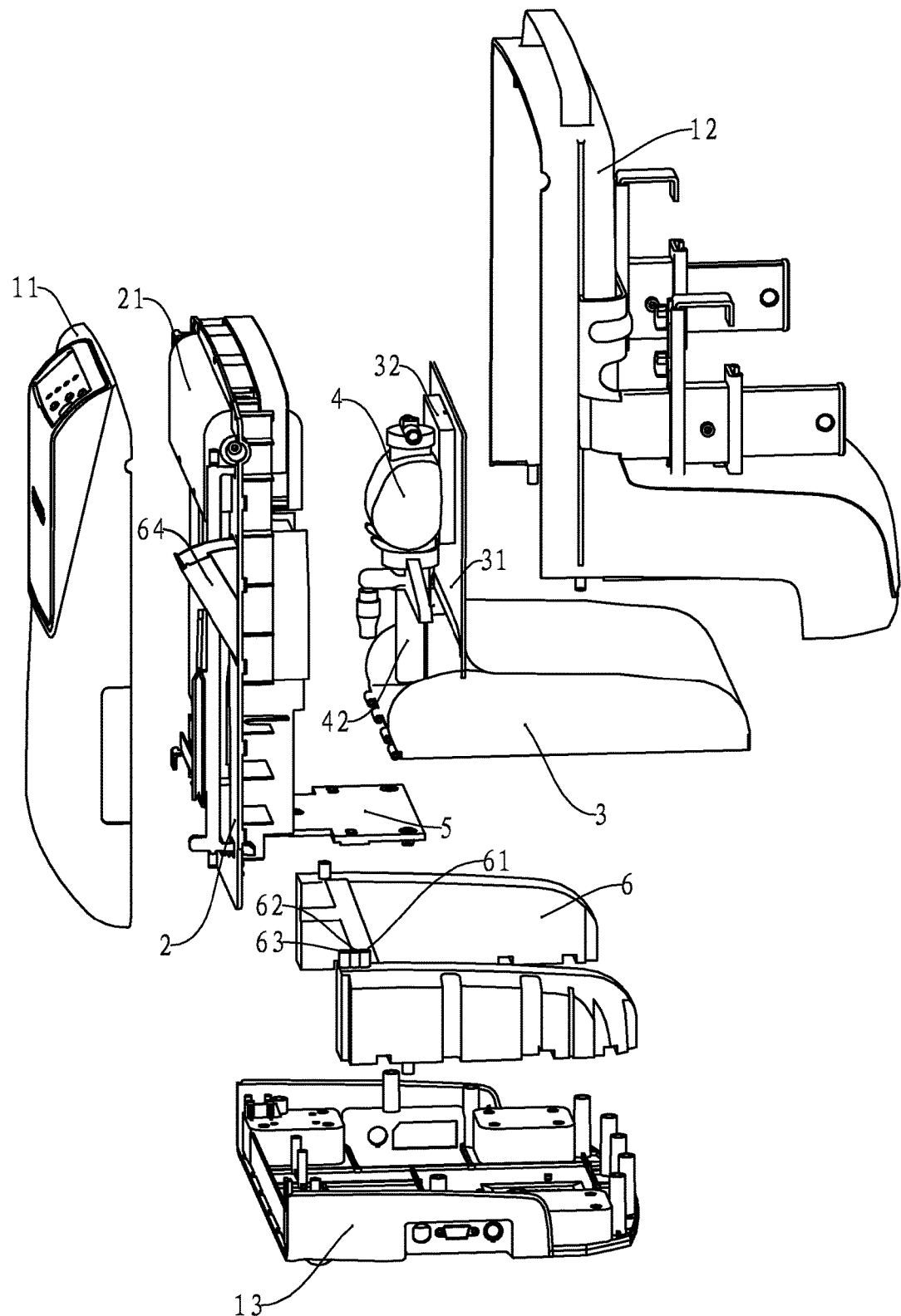
FIG. 4 is a structural diagram of the embodiment of the dynamic urine monitor of the invention.

The inner structure of the dynamic urine monitoring instrument 100 is shown in FIG. 4. Inside the case is equipped the supporting frame 2; the supporting frame 2 is fixed with the rear shell 12 and the bottom shell 13. A compartment 21 is set on the top portion of supporting frame 2. Inside the compartment 21 there are a water pump and a density meter. The inner structure of the compartment 21 will be discussed in details later. The bottom portion of the compartment 21 has a weighing box 3. On the vertical wall 31 of the weighing box 3 is equipped a urine collection device 4 without showing the urine pipeline linking to the patient. The urine pipeline introduces the urine to the urine collection device 4. The urine collection device 4 is set on the vertical wall 31 via a fixing device 32. The flexible main container 42 of the urine collection device 4 can be bent over to fit in the inner compartment of weighing box 3. The weighing box 3 is placed on the weight sensor through the platform 5. It can be understood that the weight sensor can also be s spring-type weight sensor and the urine collection device or the weighing box which contains the urine collection device can hang under the weight sensor.

Above the bottom shell 13 there are two water tanks 6, one on each side; these two water tanks are linked by a tube. The water tank on the right has a water inlet 61, water outlet 62, and water level measurement entrance 63; the relative positions of them are not limited to what are showed in FIG. 4 and they can be located on any convenient positions. The supporting frame 2 is equipped with a moveable or rotatable water entrance 64 which is used to add clean water to the water tank. When water is added, the moveable or rotatable water entrance 64 stays open; and when the water addition is complete, it stays closed and on the level of the supporting frame 2. FIG. 4 shows the status where the water entrance 64 stays open. The water entrance 64 is linked through tubes with the water inlet 61 and water outlet 62 of the water tank 6 and the water pump; two measurement electrodes are inserted into the water tank 6 through the water level measurement entrance 63 to measure the water level in the water tank 6. When the water level in the water tank 6 reaches or goes below a critical level, the alarm which is linked with the measurement electrodes will sound a warning, indicating the water tank 6 needs more clean water.

Figure 5:
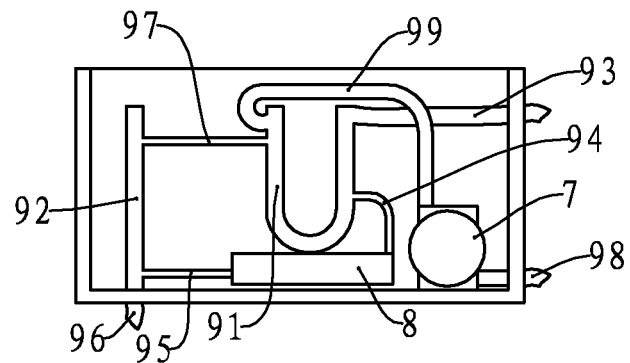
FIG. 5 is an illustrative diagram of the pipeline structure of the embodiment of the dynamic urine monitor of the invention.

As shown in FIG. 5, the inside of the compartment is equipped with a water pump 7, density meter 8, U tube 91 and vertical tube 92; connecting tubes 93, 94, 95, 96, 97, 98, and 99 as a part of the pipeline are respectively linked with one or more of the pump 7, density meter 8, U tube 91 and vertical tube 92. Inside the density meter 8 there are a density sensor and a density information Analogue-to-Digital Converter (ADC).

Figure 6:
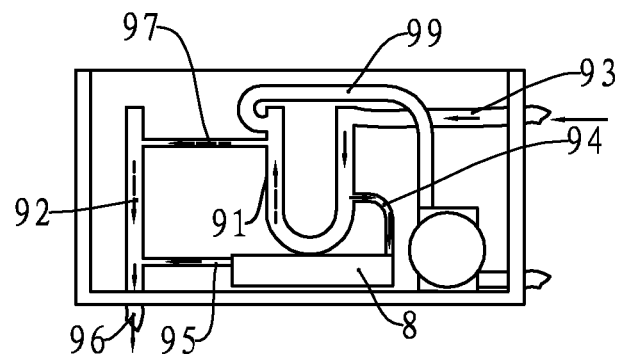
FIG. 6 is an illustrative flow diagram of the pipeline of the embodiment of the dynamic urine monitor of the invention.

As shown in FIG. 6, the patient's urine enters through the connecting tube 93 into the U tube 91, and then through the connecting tube 94 enters into the density meter 8. After the density measurement, the urine exits through the connecting tube 95 to the vertical tube 92, and then flows through the connecting tube 96 to the urine collection device. When the patient's urine flow is too high, the urine level in the U tube 91 exceeds the exit which connects with the connecting tube 97, a portion of the urine flows through the connecting tube 97 into the vertical tube 92, and then flows through the connecting tube 96 into the urine collection device. Thereby, the connecting tube 97 and the vertical tube 92 form an overflow path in parallel with the density meter 8. When the urine level in the U tube cannot reach the exit between the connection of the U tube 91 and the connecting tube 97, the urine will only flow through the connecting tube 94 into the density meter 8, and then flow into the urine collection device through the connecting tube 95, vertical tube 92 and the connecting tube 96.

Figure 7:
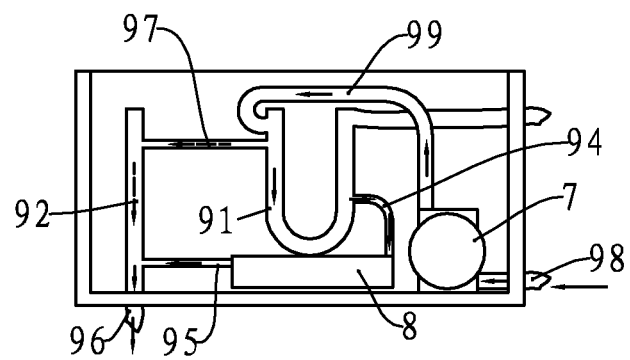
FIG. 7 is an illustrative diagram of water flow of the embodiment of the dynamic urine monitor of the invention.

In general, when a measurement is completed, the density meter 8 is flushed with water. As shown in FIG. 7, during flushing, the water pump 7 is on; the clean water of the water tank flows through the connecting tube 98 into the water pump 7, and then through the connecting tube 99 into the U tube 91. When the water level in the U tube 91 is lower than the exit which connects with the connecting tube 97, water only flows through the connecting tube 94 into the density meter 8, and then flows into the urine collection device through the connecting tube 95, the vertical tube 92 and the connecting tube 96.

Figure 8:
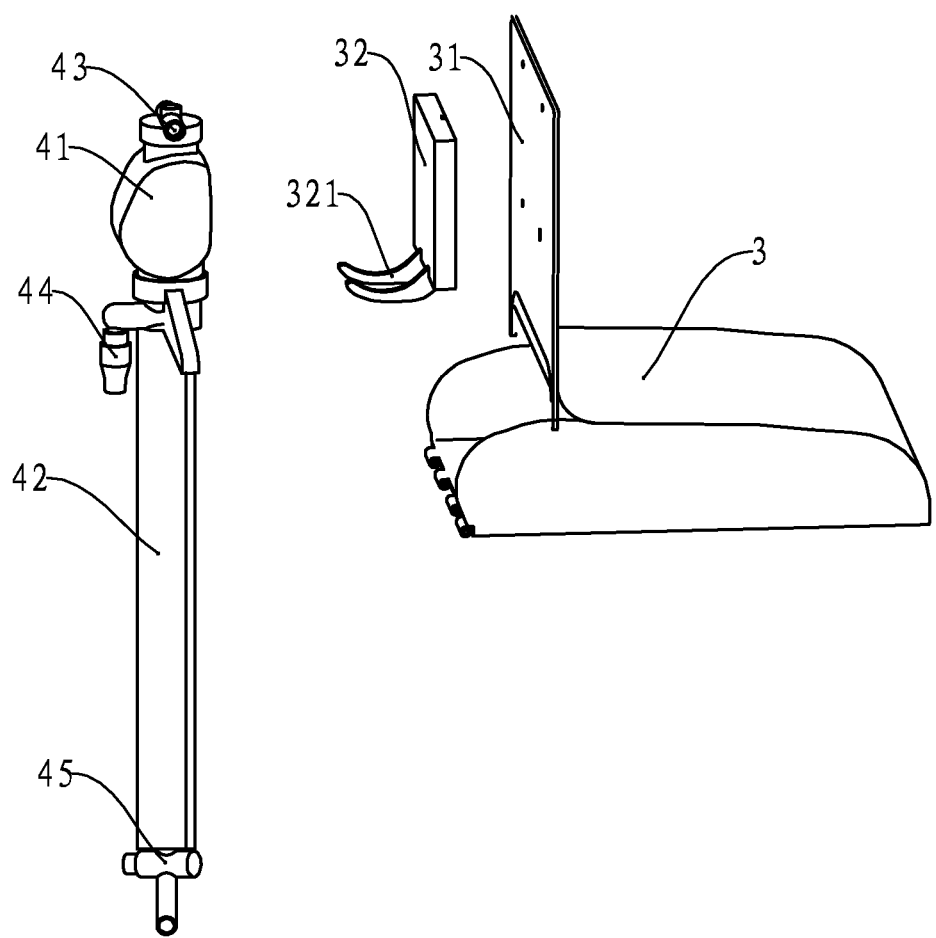
FIG. 8 is an exploded view of the urine collection device and the weighing box of the embodiment of the dynamic urine monitor of the invention.

The fixing mechanism and structure of the urine collection device are as follows. As shown in FIG. 8, the urine collection device 4 comprises a first container 41 which is made from a rigid material and a second container 42 which is made from a flexible material. The fixing plate 32, which is used to fix the urine collection device 4, is fixed on the vertical wall 31 of the weighing box 3. Below the fixing plate 32 there are two supporting frames 321 which coordinate with the frame of the first container 41 to place the urine collection device 4 detachably on the supporting frames 321. The urine collection device 4 has a tube inserting hole 43 and the bottom end of the tube 96 (not shown in FIG. 8) is inserted into the tube inserting hole 43. The first container 41 has a valve 44 for convenient urine sampling. Inside the first container 41 there is a reversed U tube; one end of the reversed U tube is connected with the second container 42, and another end extends to the bottom of the first container 41. When the urine in the first container 41 reaches the designed level, the urine level reaches the top of the reversed U tube, and thus the reversed U tube is connected through. Through the approval function, the urine in the first container 41 will completely transferred into the second container 42. Therefore, the first container 41 does not have urine which sits there for too long. When urine is sampled through the valve 44, the samples are fresh, which can accurately reveal the health status of the patient. The second container 42 has a valve 45 on the bottom portion to release the urine in the second container 42 and water which was used to flush the density meter.

Inside the case there is a master control module, power source, transformer, wire and tube etc. to ensure the system to work properly. In addition, the urine tube inserting hole is equipped with a temperature sensor.

Figure 9:
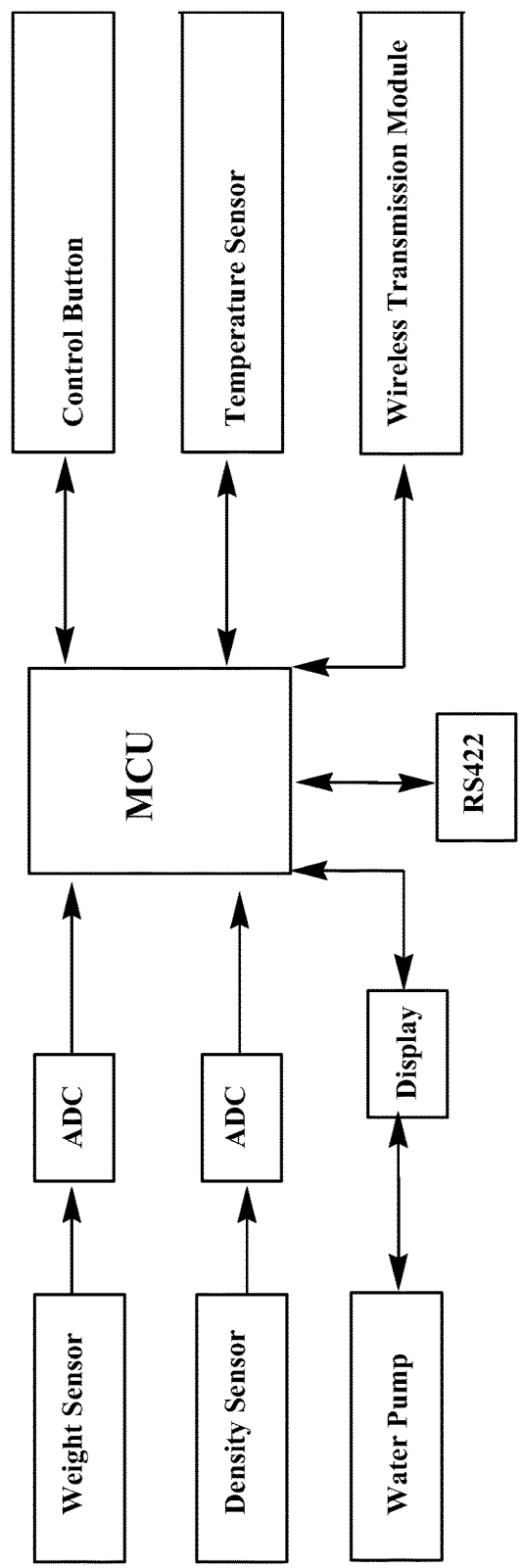
FIG. 9 is a signal structural diagram of the embodiment of the dynamic urine monitor of the invention.

The signal structural diagram of the dynamic urine monitor is shown in FIG. 9. The master control module is a central control system such as a Microcontroller Unit (MCU). It is used to manage the weight sensor, density sensor, temperature sensor, control push-button, water pump and wireless transmission module etc. Besides wireless transmission module, the outlet-inlet module can also use RS232, RS422 and USB etc.

The weight sensor and the temperature sensor can be those available on the market which can continuously measure temperature and weight. The density meter comprises a density sensor and a density information Analogue-to-Digital Converter (ADC). It uses MEMS to measure the refraction index of the liquid and to calculate the density of the liquid. MEMS means Micro-Electro-Mechanical Systems. MEMS are available in volume production; they refer to integrated micro systems, micro sensors, micro actuators and other micro machines or systems which integrate signal processing, control circuit, interface, communication and power. MEMS have been developed as a result of the development of the micro processing technology of the semiconductor integrated circuits and the super precise mechanical processing technology. Currently, MEMS have been widely used in micro-fluidic chips, synthetic biology and other areas. The micro system, micro sensor and electronic components of the MEMS are integrated to perform the measurement tasks; the measurement results, after they are treated by the ADC and the monolithic integrated circuit, are transmitted to the outside as data information of the density data. The density data are transmitted to outside via RS232. The advantages of using MEMS are to give high data accuracy, to have small size, to respond quickly, and to continuously perform the on-line measurements.

The dynamic urine monitor has the following working modes: debugging control mode, normal working mode, and data recording mode. The debugging mode is used to test or debug the measurement system. The normal working mode is the default working mode of the dynamic urine monitor. Under the normal working mode, all modules of the measurement system perform their normal functions and the real-time measurement of the patient's urine. Only when the dynamic urine monitor is not connected with the outside or the connection is broken, the dynamic urine monitor enters into the data recording mode. Under the data recording mode, the master control module of the dynamic urine monitor shuts down its outgoing communication program, turns on the data recording program, and stores the data in the storage element of the master control module. The various working modes' alternation is controlled by the master control module. The default working mode of the measurement system is the normal working mode.

The dynamic urine monitor 100 can work independently. For instance, the dynamic urine monitor can be moved to a given patient's room without connecting into the network. Without a connection to the outside, the measured data of the dynamic urine monitor cannot be treated and displayed. Without connecting to the outside, the dynamic urine monitor may independently keep the data for two hours; after two hours, the data may disappear.

Embodiment of the Dynamic Urine Monitoring Instrument

In this embodiment, the dynamic urine monitoring instrument comprises a separable dynamic urine monitor and a treatment device. The data communication between the dynamic urine monitor and the treatment device is performed by a wireless transmitting mode. Therefore, the data treatment device can be placed in any convenient place in the patient's room. It can be understood that the treatment device can be attached to the dynamic urine monitor. Alternatively, the data communication between the dynamic urine monitor and the treatment device can be performed through a wire transmitting mode.

In this embodiment, the dynamic urine monitor can be those which are discussed above. The treatment device is connected with a dynamic urine monitor. It can be understood that a treatment device may receive data from several dynamic urine monitors, perform respective calculations and display results.

Inside the treatment device is equipped with a treatment system. The treatment system comprises an information receiving module, a data treatment module, a display monitor and a remote management module. The treatment system can work independently or be connected to a local network. Without the dynamic urine monitor, the treatment system cannot receive the measurement data. To perform a complete real-time monitoring, both the dynamic urine monitor and the treatment device must be turned on and the communication path between them must be open. The treatment device may comprise a patient's profile recording function.

If a remote management function is desirable, the treatment device can be connected to a local network by wire or WiFi. The main machine for the remote management needs to install remote management software so that the treatment device can be discovered by the main machine for remote management.

Figure 10:
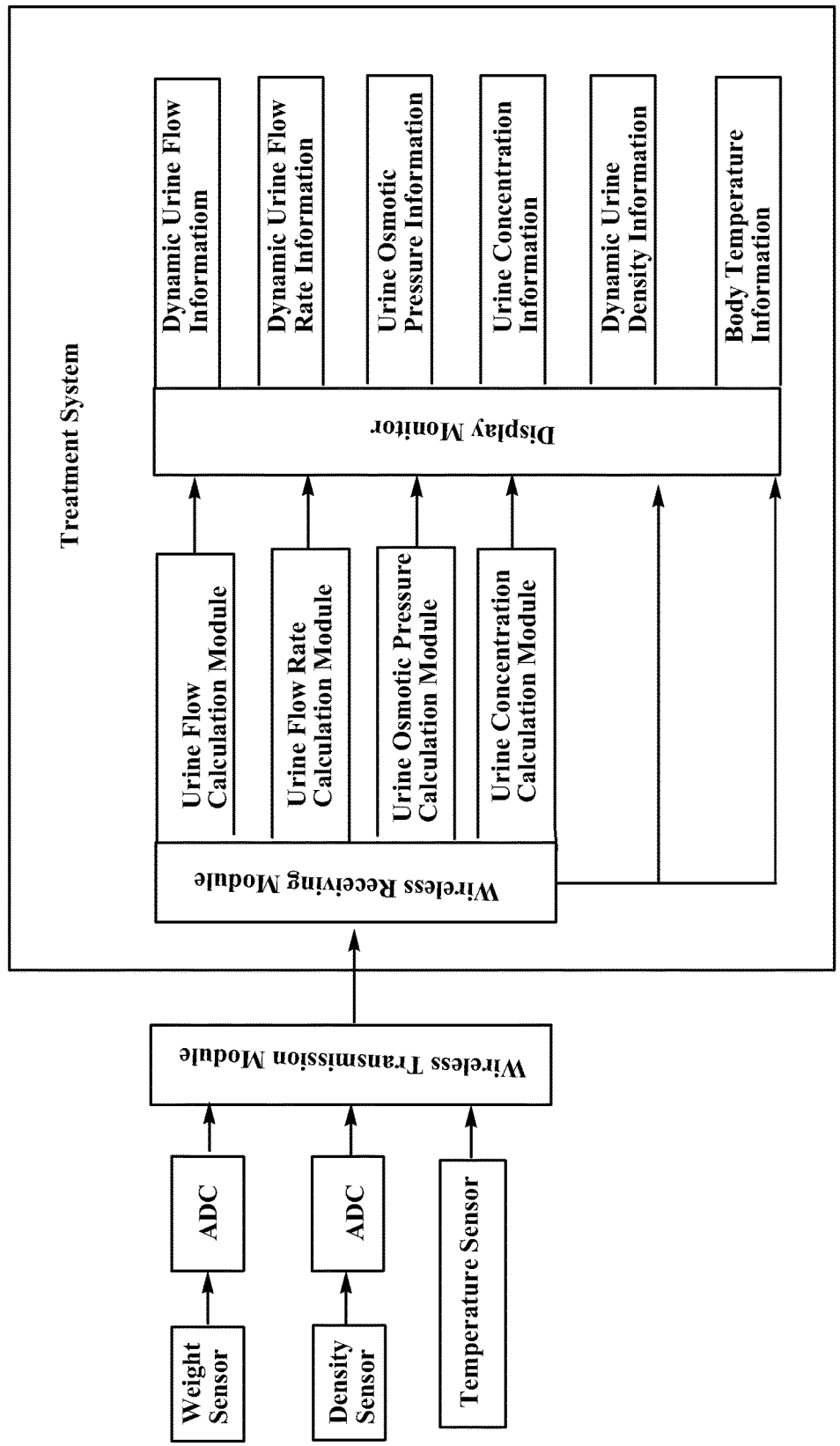
FIG. 10 is an information processing flow diagram of the embodiment of the dynamic urine monitor of the invention.

FIG. 10 shows the information processing diagram of this embodiment.

The patient's urine flows into the dynamic urine monitor; it flows through the density sensor and enters into the urine collection device. The density sensor continuously transmits information to the wireless transmitting module. The weight sensor measures the weight of the urine in the urine collection device; it continuously transmits the signals and translates the monitoring signals into data signals via the weight information transformation module, and it sends the data signals to the wireless transmitting module. At the same time, the wireless transmitting module also receives information from the temperature sensor and then sends it to the treatment module via wireless transmitting. The information receiving module inside the treatment system of the treatment device receives the urine weight, urine density and urine temperature data and sends them to the data treatment module and the display monitor. The urine temperature information and the urine density information are directly displayed on the display monitor, while the urine flow, urine flow rate, osmotic pressure and urine concentration are obtained via calculations by the relevant sub-modules of the data treatment module based on the urine weight data and the urine density data; the calculation results of the data treatment module are then shown on the display monitor.

The urine flow information is calculated based on the urine weight data and the urine density data; dividing the urine weight by the urine density results in the urine rate. The data from the weight sensor, density sensor, and temperature sensor are collected every 10 ms. The collecting periods of each sensor may vary based on need. According to the real-time measurements of the weight sensor and the density sensor and the continuous calculations of the urine flow calculation sub-module, the dynamic urine flow information continuously shows on the display monitor.

The urine flow rate is obtained by differentiating the urine flow. The calculation results produced by the urine flow calculation sub-module are transmitted to the urine flow rate calculation sub-module, and the urine flow rate calculation sub-module transmits its calculation results to the display monitor. As the urine flow calculation sub-module and the urine flow rate calculation sub-module continuously perform the calculations, the dynamic urine flow rates continuously show on the display monitor.

The urine osmotic pressure and the urine concentration are calculated based on the urine density. The calculation method follows those disclosed in the "Urine Dynamics Examination Operation Guide (Chinese Medical Association Urological Surgery Branch 2010 Edition)" and in the "ICU Question Analysis." The reference method is programmed. The urine osmotic pressure calculation sub-module and the urine concentration sub-module perform the relevant calculations based on the density data; the calculation results are displayed on the display monitor as the urine osmotic pressure information and the urine concentration information, respectively.

To use the dynamic urine monitor 100, the following procedure is followed: fixing the fixing device 15 of the dynamic urine monitor 100 on a bottom crossbeam of the patient's bed; opening the front cover gate 11 of the dynamic urine monitor 100 to install a urine collection device 4; inserting the low end of tube 96 into the tube inserting hole 43 of the urine collection device 4; turning on the power to allow the dynamic urine monitor 100 and the treatment device to work; pushing the control button 113 to return the weight sensor to the original position, i.e., resetting the sum of the urine collection device 4 and the weighing box 3 to zero; and then inserting the patient's urine tube into the urine tube inserting hole 14. The dynamic urine monitor 100 will therefore start to work. The patient's urine flows through the connecting tube 93, U tube 91, and connecting tube 94, density meter 8, and connecting tube 96 into the urine collection device 4. When the urine flows through the temperature sensor and the density sensor 8, the urine temperature and urine density are measured. The weight sensor measures the weight. The respective information passes the corresponding information ADC and is transferred to the treatment device via the wireless transmitting module. After the information receiving module inside the treatment device receives the data, it transfers the data to the data treatment module; the display monitor then displays the urine density information and temperature information, and the calculated urine flow information, urine flow rate information, urine osmotic pressure information and urine concentration information.

When the dynamic urine monitor 100 is working, the front cover gate 11 is kept open to reveal the valve 44 and to sample from the urine collection device 4. The first container 41 of the urine collection device 4 has precise scale divisions and thus it can tell from the urine collection device 4 the precise amount of the urine sample. The amount of urine sample can also be calculated based on the urine weight information shown on the display monitor.

When a monitoring period is over, the connecting urine tube is disconnected from the patient. The density meter is flushed via pushing the button 113. The waste water is also collected in the urine collection device 4. When flushing is complete, the power is turned off and the urine collection device 4 is removed.

The scope of the invention should not be limited to the preferred embodiment, for instance, the fixing device can be equipped on a center part of the back shell; only one supporting pole is used; the master control module can store more than two hours of data; the data collection period of the sensors differs from 10 ms; the data treatment module comprises a urine osmotic pressure calculation sub-module or a urine concentration calculation module, or both; and the dynamic urine monitoring device is equipped with a sensor for measuring the environmental temperature and etc.

INDUSTRY APPLICABILITY

According to the schemes of the dynamic urine monitoring instrument of the invention, the urine is introduced into the dynamic urine monitor; when it flows through the density sensor, the dynamic density information is obtained; when it flows into the urine collection device, the urine weight information is obtained. The above density information and the weight information pass through the weight information transformation module and the density information transformation module, respectively, to convert the monitoring signals into data signals which are then exported to treatment device via the outlet-inlet module. After the information receiving module of the treatment device receives the data and sends the data to the treatment module, the urine flow calculation sub-module of the data treatment module calculates the urine flow information based on the urine weight data and the urine density data and display the urine flow information on the display monitor. At the same time, the display monitor also displays the urine density information without calculation. Nurses and doctors can directly observe the urine flow and urine density information of the patient, discover abnormalities and make a treatment plan for the patient.

What is claimed is:

1. A dynamic urine monitor comprising a case, inside of said case being equipped with:
    a urine collection device;
    a pipeline for flowing urine to the urine collection device;
    a measurement system comprising a weight measurement subsystem, said weight measurement subsystem comprising a weight sensor and a weight information Analogue to Digital Converter (ADC); said weight sensor being connected with the urine collection device; wherein the measurement system further comprises a density measurement subsystem; said density measurement system comprising a density sensor and a density information ADC; said density sensor being used to dynamically measure urine density and being serially connected to said pipeline in the upstream of the urine collection device; and
    an input-output module for carrying on data exchange for the weight information ADC and the density information ADC with outside;
    wherein the pipeline comprises an overflow path which is parallel-linked with the two ends of the weight sensor.

2. The dynamic urine monitor of claim 1, wherein the measurement system further comprises a master control module; said master control module is equipped with a storage element for storing the information from the weight information ADC and the density information ADC.

3. The dynamic urine monitor of claim 2, wherein inside the case is equipped with a washing device; said washing device comprises a water pump; said water pump is connected with a water inlet pipe and a water outlet pipe; and said water outlet pipe is connected with the density sensor.

4. The dynamic urine monitor of claim 3, which comprises a water container, said water container is placed inside the case and is connected with the water inlet pipe.

5. The dynamic urine monitor of claim 4, wherein inside the water container is equipped with a water level detector; and said water level detector is connected with an alarm device.

6. A dynamic urine monitor comprising a case, inside of said case being equipped with:
    a urine collection device;
    a pipeline for flowing urine to the urine collection device;
    a measurement system comprising a weight measurement subsystem, said weight measurement subsystem comprising a weight sensor and a weight information Analogue to Digital Converter (ADC); said weight sensor being connected with the urine collection device; wherein the measurement system further comprises a density measurement subsystem; said density measurement system comprising a density sensor and a density information ADC; said density sensor being used to dynamically measure urine density and being serially connected to said pipeline in the upstream of the urine collection device; and
    an input-output module for carrying on data exchange for the weight information ADC and the density information ADC with outside;
    whether the dynamic urine monitor further comprises a fixing device; said fixing device comprises a fixing clip which hangs on a crossbeam of a patient's bed; and a guiding mechanism is set on the case which guides said fixing device to freely slide in a vertical direction; wherein the fixing device comprises:
a sliding board and said sliding board slides within the guiding mechanism;
a supporting pole; one end of said supporting pole is fixed on the sliding board and is placed horizontally; said fixing clip can horizontally slide along said supporting pole; and
a first fixing knob for fixing the fixing clip on said supporting pole.

7. The dynamic urine monitor of claim 6, wherein both sides of the case are equipped with the guiding mechanisms; both ends of the sliding board are respectively restricted within the guiding mechanisms on both sides of the case; and there equipped with symmetric supporting poles, fixing clips, and first fixing knobs.

8. The dynamic urine monitor of claim 7, wherein the fixing clip is equipped with a second fixing knob.

9. The dynamic urine monitor of claim 6, wherein the bottom of the case is equipped with rolling wheels.

10. The dynamic urine monitor of claim 2, wherein the urine collection device comprises a first container locating on the upstream and a second container locating on the downstream; said first container is connected with the second container through an inner reversed U-shaped tube; and the first container is equipped with a valve for discharging the urine from the first container.

11. The dynamic urine monitor of claim 10, wherein the case is equipped with a front cover gate which faces said valve.

12. The dynamic urine monitor of claim 2, wherein the measurement system further comprises a temperature measurement subsystem; said temperature measurement subsystem comprises a temperature sensor; and said temperature sensor is equipped on the entrance of the pipeline.

13. A dynamic urine monitoring instrument, comprising:
a treatment device comprising an information receiving module; a display monitor, and
at least one dynamic urine monitor; wherein said dynamic urine monitor comprises a case; inside said case is equipped a urine collection device, a pipeline, and a measurement device; said urine collection device is used to collect urine; said pipeline is used to flow the urine into the urine collection device; said measurement device comprises a weight measurement subsystem; said weight measurement subsystem comprises a weight sensor and weight information Analogue to Digital Converter (ADC); said weight sensor is connected with said urine collection device; wherein said measurement system further comprises a density measurement subsystem; said density measurement subsystem comprises a density sensor and a density information ADC; said density sensor is used to measure the urine density and is serially connected into the upstream pipeline of the urine collection device; wherein the pipeline comprises an overflow path which is parallel-linked with the two ends of the weight sensor;
an outlet-inlet module; said outlet-inlet module is used for carrying on data exchange between the weight information ADC and the density information ADC with the information receiving module;
wherein said treatment device performs calculations based on the information received by the information receiving module; the calculations comprise a urine flow calculation; and
wherein said display monitor displays the urine density information received by the information receiving module and the calculation results of the treatment device.

14. The dynamic urine monitoring instrument of claim 13, wherein the outlet-inlet module is a wireless transmitting module; and the information receiving module is a wireless receiving module.

15. The dynamic urine monitoring instrument of claim 13, wherein the calculations comprise a urine osmotic pressure calculation.

16. The dynamic urine monitoring instrument of claim 14, wherein the calculations comprise a urine flow rate calculation and a urine concentration calculation.

17. The dynamic urine monitoring instrument of claim 13, wherein said treatment device is remotely managed by a main machine for remote management.

18. The dynamic urine monitoring instrument of claim 13, wherein said treatment device is used for storing the information received by the information receiving module and the history of the calculation results.

19. The dynamic urine monitoring instrument of claim 13, wherein the pipeline comprises:
a U tube;
a vertical tube having an outlet for flowing the urine to the urine collection device;
a first connecting tube having an inlet for introducing the urine, and an outlet in communication with the U tube;
a second connecting tube having an inlet in communication with the U tube, and an outlet in communication with an end of the weight sensor;
a third connecting tube having an inlet in communication with an other end of the weight sensor, and an outlet in communication with the vertical tube; and
a fourth connecting tube having an inlet in communication with the U tube, and an outlet in communication with the vertical tube;
wherein the inlet of the fourth connecting tube is higher than the inlet of the second connecting tube in a vertical position; and
the U tube, the fourth connecting tube and the vertical tube form the overflow path.

20. The dynamic urine monitor of claim 1, wherein the pipeline comprises:
a U tube;
a vertical tube having an outlet for flowing the urine to the urine collection device;
a first connecting tube having an inlet for introducing the urine, and an outlet in communication with the U tube;
a second connecting tube having an inlet in communication with the U tube, and an outlet in communication with an end of the weight sensor;
a third connecting tube having an inlet in communication with an other end of the weight sensor, and an outlet in communication with the vertical tube; and
a fourth connecting tube having an inlet in communication with the U tube, and an outlet in communication with the vertical tube;
wherein the inlet of the fourth connecting tube is higher than the inlet of the second connecting tube in a vertical position; and
the U tube, the fourth connecting tube and the vertical tube form the overflow path.

* * * * *